United States Patent [19]

Sasayama et al.

[11] Patent Number: 5,731,505

[45] Date of Patent: Mar. 24, 1998

[54] INBRED BROCCOLI LINE SA-5

[75] Inventors: Junichi Sasayama, Shizuoka; Shigetoshi Kobayashi, Mie, both of Japan

[73] Assignee: Sakata Seed America, Inc., Morgan Hill, Calif.

[21] Appl. No.: 727,150

[22] Filed: Oct. 8, 1996

[51] Int. Cl.[6] .................... A01H 5/00; A01H 4/00

[52] U.S. Cl. .................... 800/200; 800/205; 800/250; 800/255; 800/DIG. 15; 47/DIG. 1

[58] Field of Search .................... 800/200, 205, 800/250, 255, DIG. 15; 47/DIG. 1

[56] References Cited

PUBLICATIONS

Alpuche–Solis et al. Assessment of glucosinolates in broccoli by three different methodologies. Journal of Food Biochemistry. vol. 16, pp. 265–275 (Abstract only), 1993.

Hansen et al. Regeneration of plants from protoplasts of rapid–cycling Brassica oleracea. Plant Cell Report. vol. 13, pp. 335–339. (Abstract only), 1994.

*Primary Examiner*—Douglas W. Robinson
*Assistant Examiner*—Melissa L. Kimball
*Attorney, Agent, or Firm*—Rothwell, Figg, Ernst & Kurz, pc

[57] ABSTRACT

An inbred broccoli line, designated SA-5, is disclosed. The invention relates to the seeds of inbred broccoli line SA-5, to the plants of inbred broccoli line SA-5 and to methods for producing a broccoli plant produced by crossing the inbred line SA-5 with itself or another broccoli line. The invention further relates to hybrid broccoli seeds and plants produced by crossing the inbred line SA-5 with another broccoli line.

13 Claims, No Drawings

§ 1
INBRED BROCCOLI LINE SA-5

BACKGROUND OF THE INVENTION

This invention relates to a new and distinctive broccoli inbred line, designated SA-5. There are numerous steps involved in the development of any new and novel, desirable plant germplasm with superior combining ability. Plant breeding begins with the analysis and definition of problems and weaknesses of the current germplasm, the establishment of program goals, and definition of specific breeding objectives. The next step is selection of germplasm that possess the traits to meet the program goals and the best breeding method to reach those goals. The objective is to combine in a single variety or hybrid an improved combination of desirable traits from the parental germplasm. These important characteristics may include higher yield, better flavor, improved color and field holding ability, resistance to diseases and insects along with economic seed yields to facilitate the cost of hybrid seed production.

The method chosen for breeding or selection depends on the mode of plant reproduction, the heritability of the trait(s) being improved, and the cultivar (variety) used commercially (e.g. $F_1$ hybrid, pureline). The complexity of inheritance influences choice of breeding method. One method of identifying a superior plant is to observe its performance relative to other experimental plants and to a widely grown standard cultivar. If a single observation is inconclusive, observation in multiple locations and seasons provide a better estimate of its genetic worth.

The development of commercial broccoli hybrids requires the development of homozygous inbred lines. Breeding programs combine desirable traits from two or more germplasm sources from which various broad based breeding gene pools are used to develop inbred lines by selfing followed by selection of desired phenotypes sometimes utilizing anther, microspore and ovule culture to speed up and improve selection efficiency.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior broccoli cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same broccoli traits.

Description of breeding methods that are commonly used for different traits and crops can be found in one of several reference books (e.g., Allard, 1960; Simmonds, 1979; Sneep et al., 1979; Fehr, 1987).

Proper testing and evaluation should detect any major faults and establish the level of superiority or improvement over current cultivars. In addition to showing superior performance, there must be a demand for a new cultivar that is compatible with industry standards or which creates a new market. For seed-propagated cultivars, it must be feasible to maintain the inbred lines and produce seed easily and economically.

Broccoli is a new crop in North, South and Central America, Europe and Asia. The introduction of hybrid cultivars in the 1960's provided a magnitude increase in yield, holding ability, expanded growing seasons and large scale production of broccoli. The goal in broccoli breeding is to make continued improvement in hybrid broccoli yields and horticultural characteristics in order to sustain the supply to meet continuous increase in demand for broccoli in developed and emerging world economies. To accomplish this goal new breeding methods such as anther culture and microspore culture have been utilized to more rapidly generate inbred broccoli lines from more diverse germplasm sources.

Broccoli (*Brassica oleracea*, Italica group) belongs to the mustard family. All *Brassica oleracea* will cross pollinate. Pollination is effected by insect vectors, most common of which is the honey bee. Broccoli, like most other Brassica, have a genetic characteristic of self incompatibility which encourages cross pollination resulting in higher levels of variability. Variability in populations is desired for wide adaptation and survival. Broccoli breeding populations can be inbred or backcrossed for 8 to 9 generations and/or with the use of double haploids derived from anther culture to develop homozygous inbred lines. Broccoli $F_1$ hybrids can be produced by using self-incompatibility or cytoplasmic male sterility to control pollen movement between selected inbred lines.

Self-incompatibility is a breeding system that enforces outcrossing and therefore maximizes recombination in cross pollinated species. This breeding system in nature has been utilized by man in $F_1$ hybrid breeding, especially in Brassica vegetables (Tsunoda et al., 1981, chapter 13). The stigma of Brassica flowers is the site of the incompatibility reaction. Compatible pollen tubes pierce the cuticle layer of the stigma and grow down the style tissue. When incompatible pollen grains germinate on the stigma, some pollen tubes can penetrate the cuticle layer but the penetrated tubes cannot grow down the style. "Bud pollination" is done to overcome the self-incompatibility in order to maintain inbred broccoli lines. Young buds of inbred broccoli, and other Brassica, can be fertilized by incompatible (self) pollen. The young stigmas, unlike mature stigmas, cannot discriminate between compatible and incompatible pollen. Therefore bud pollination by hand will produce selfed seed on inbred broccoli and maintains the self-incompatibility needed for hybrid seed production.

Male sterility is another method used in Brassica vegetable species to produce $F_1$ hybrids. This method of producing hybrids in Brassica is a more recent development compared to self-incompatibility.

The plants associated with the Brassica group have been familiar to mankind since ancient times, and always of great agricultural importance. Brassica is a major food species worldwide. Brassica species have a general adaptation for cool climate growing conditions. Therefore, adaptation has occurred for summer growing conditions with cool to moderate climates and for winter growing conditions in warmer or tropical locations.

SUMMARY OF THE INVENTION

The invention comprises a novel inbred broccoli line, designated SA-5. This invention thus relates to the seeds of inbred broccoli line SA-5, to the plants of inbred broccoli line SA-5, to methods used for controlling pollination when making hybrid seed with SA-5, and to methods for producing a broccoli plant by crossing the inbred broccoli line SA-5 with itself or another broccoli line. This invention further relates to hybrid broccoli seeds and plants produced by crossing the inbred line SA-5 with another broccoli line.

DETAILED DESCRIPTION OF THE INVENTION DEFINITIONS

In the description and tables which follow, a number of terms are used. In order to provide a clear and consistent understanding of the specification and claims, including the scope to be given such terms, the following definitions are provided:

Maturity. Plants are considered mature when the head and stem have developed to the fresh market maturity stage.

Yield. The yield is the weight in grams for a harvested broccoli head or floret cluster.

Overall Rating Score. This Overall Rating Score is rated on a scale of 1 to 5. A score of 5 indicates an excellent overall rating. A score of 3.0 indicates average, and a score of 1 indicates poor.

Color. Color means the color of the head at maturity.

Field Holding Ability. Field Holding Ability means the ability of a plant to maintain good head quality (i.e., small, firm, green heads) after the optimal harvest date.

Disease and Insect Ratings. Disease and Insects are rated on a scale of 1 to 5. A score of 5 indicates severe damage. A score of 3.0 indicates moderate damage, and a score of 1 indicates no damage.

Inbred broccoli SA-5 is a heading broccoli (Brassica oleracea Italica group) with superior characteristics, and provides an excellent parental line in crosses for producing first generation ($F_1$) hybrid broccoli.

Inbred broccoli SA-5 was developed by selfing from the hybrid Broccoli Samurai and using pedigree selection method at the Sakata Seed Corporation research station in Kimitsu Japan.

The inbred has shown uniformity and stability for all traits, as described in the following variety description information. The line has been increased by self (bud) pollination with continued observation for uniformity.

The inbred broccoli line SA-5 has the following morphologic and other characteristics.

VARIETY DESCRIPTION INFORMATION

1. MATURITY: Very late, 100+ days
2. PLANT CHARACTERISTICS:
   Habit: Spreading
   Plant Height: 32 cm
   Leaves: 27 cm average length at mid-point of the plant, 16 cm width at mid-point of the plant, 2:1 length to width ratio
   Leaf Margins: Wavy
   Veins: Thin
   Petiole Length: 16 cm
   Petiole Attachment: Petiolate
   Anthocyanin Coloration: No coloration
   Inflorescence: Medium flower bud size, yellow flowers, few marketable side sprouts after head harvest, 15 cm center head diameter, 10 cm center head depth, 4 cm diameter of stem base of head, medium compactness of center head, medium green center head color.

This invention is also directed to methods for producing a broccoli by crossing a first parent broccoli plant with a second parent broccoli plant, wherein the first or second broccoli plant is the inbred broccoli from the line SA-5. Further, both first and second parent broccoli plants may be from the inbred line SA-5. Therefore, any methods using the inbred broccoli line SA-5 are part of this invention: selfing, backcrosses, hybrid breeding, and crosses to populations. Any plants produced using inbred broccoli line SA-5 as a parent are within the scope of this invention. Advantageously, the inbred broccoli line is used in crosses with other broccoli varieties to produce first generation ($F_1$) broccoli hybrid seed and plants with superior characteristics.

As used herein, the term "plant" includes plant cells, plant protoplasts, plant cell of tissue culture from which broccoli plants can be regenerated, plant calli, plant clumps, and plant cells that are intact in plants or parts of plants, such as pollen, flowers, seeds, stalks, stumps, leaves and the like. Thus, another aspect of this invention is to provide for cells which upon growth and differentiation produce the inbred broccoli SA-5.

SA-5 is most similar to hybrid broccoli Samurai, however, there are numerous differences including the fact that SA-5 is shorter and SA-5 produces less side shoots.

Some of the criteria used to select the broccoli in various generations include higher yield, better flavor, improved color and field holding ability, resistance to diseases and insects.

TABLES

In the tables that follow, the traits and characteristics of inbred broccoli line SA-5 are given in hybrid combination. The data collected on hybrids containing inbred broccoli line SA-5 as one parent is presented. The tables present overall rating scores and additional characteristics. SA-5 was tested in several hybrid combinations at numerous locations, with two or three replications per location. Information about these hybrids, as compared to several check hybrids, is presented.

In column 1, the genotypes are listed and the second genotype listed in row 2 is another hybrid. Column 2 shows the overall rating which ranges from 1–5, with 5 being the best overall rating. Column 3 lists various characteristics of the specific hybrid.

TABLE 1

| Kimitsu Research Station - planted 7/25/90 | | |
|---|---|---|
| Hybrid | Overall Rating | Additional Characteristics |
| SA-5 x Line Ry | 4.00 | Very vigorous plant, very smooth shape, dark green, attractive head. |
| Line T x Line RY | 3.00 | Vigorous plant, head position is bottom, small head, good uniformity. |
| Line M x Line RY | 1.00 | Leafy, very lumpy, not good. |
| SA-5 x Line 31 | 3.50 | No side shoots, thick stem, big head, high yield, vigorous. |
| Line 36 x Line 31 | 2.50 | Big and tight head, semi-dome, slightly irregular shape, dark green. |
| Line M x Line 31 | 1.00 | Very lumpy, not uniform. |

TABLE 2

| Tateyama Japan Research Station - planted 8/25/90 | | |
|---|---|---|
| Hybrid | Overall Rating | Additional Characteristics |
| SA-5 x Line 31 | 4.00 | Good dome shape, very dark green color. |
| Line G x Line 31 | 3.50 | Big head, semi-flat shape, good for processing. |

TABLE 2-continued

Tateyama Japan Research Station - planted 8/25/90

| Hybrid | Overall Rating | Additional Characteristics |
|---|---|---|
| Line I x Line 31 | 3.50 | Color is not good, semi-dome shape, big head, good for processing. |
| Line T x Line 31 | 2.00 | Purplish head. |

TABLE 3

Kimitsu Research Station in Japan - planted 8/3/92

| Hybrid | Overall Rating | Additional Characteristics |
|---|---|---|
| Line 1 x SA-5 | 4.00 | Vigorous, smooth dome shape, wide adaptability. |
| Line 38 x Line 21 | 1.50 | Small bead, irregular shape, tight, big head. |
| Line I x Line 21 | 1.00 | Irregular shape, small bead, dark green. |
| Line GD x SA-5 | 3.00 | Very smooth dome shape, vigorous, thick stem, heavy, color not good. |
| Line GD x Line F | 1.00 | Semi-flat, lumpy, loose head, not good. |
| Line G x SA-5 | 4.50 | Vigorous, smooth dome shape, slightly pale green, very good. |
| Line G x Line IK | 3.50 | Vigorous, head up, not smooth, semi-flat, lumpy, small head. |
| Line G x Line C | 2.00 | Not uniform, flat, irregular shape. |
| Line G x Line E | 1.00 | Flat, lumpy, not good, tight, dark green. |

TABLE 4

Kakagawa Research Station in Japan - planted 8/4/93

| Hybrid | Overall Rating | Additional Characteristics |
|---|---|---|
| Line G x SA-5 | 4.00 | Very smooth dome shape, big head, open habit. |
| Line G x Line 751 | 1.00 | Head is up, small bead, very lumpy. |
| Line G x Line N | 2.00 | Very open habit, dome shape |
| Line G x Line 316 | 1.00 | Tight and big head, flat shape. |
| Line G x Line 3146 | 1.00 | Very lumpy, irregular shape. |

TABLE 5

Kakagawa Research Station in Japan - planted 8/4/93

| Hybrid | Overall Rating | Additional Characteristics |
|---|---|---|
| Line G x SA-5 | 3.50 | Open habit, vigorous plant, good dome shape. |
| Line G x Line KB | 1.00 | Big bead, erect habit, semi-dome, smooth head. |

DEPOSIT INFORMATION

Inbred seeds of SA-5 have been placed on deposit with the American Type Culture Collection (ATCC), Rockville, Md. 20852, under Deposit Accession Number 97698 on Aug. 28, 1996.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. Inbred broccoli seed designated SA-5 having ATCC accession No. 97698.

2. A broccoli plant produced by growing the seed of claim 1.

3. Pollen of the plant of claim 2.

4. An ovule of the plant of claim 2.

5. An inbred broccoli plant having all the physiological and morphological characteristics of the broccoli plant of claim 2.

6. A broccoli plant regenerated from a tissue culture of tissue obtained from the broccoli plant of claim 2, said regenerated broccoli plant capable of expressing all the physiological and morphological characteristics of said broccoli plant of claim 2.

7. A method of producing first generation ($F_1$) hybrid broccoli seed comprising inbred parent of broccoli with a second inbred broccoli plant and harvesting the resultant first generation ($F_1$) hybrid broccoli seed, wherein said first or second parent broccoli plant is the broccoli plant of claim 2.

8. The method of claim 7 wherein the said broccoli plant is the female parent.

9. The method of claim 7 wherein said broccoli plant is the male parent.

10. A first generation ($F_1$) hybrid broccoli plant produced by growing said hybrid broccoli seed of claim 7.

11. The method of claim 7 wherein said broccoli hybrid seed is produced using self-incompatibility.

12. The method of claim 7 wherein the said hybrid broccoli seed is produced using male sterility.

13. Seed produced by growing the hybrid broccoli plant of claim 10.

\* \* \* \* \*